United States Patent
Miwa et al.

(10) Patent No.: US 7,101,335 B2
(45) Date of Patent: Sep. 5, 2006

(54) NON-CONTACT TYPE TONOMETER

(75) Inventors: Tetsuyuki Miwa, Aichi (JP); Hiroyuki Tashiro, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 786 days.

(21) Appl. No.: 10/055,944

(22) Filed: Jan. 28, 2002

(65) Prior Publication Data

US 2002/0103427 A1    Aug. 1, 2002

(30) Foreign Application Priority Data

| Feb. 1, 2001 | (JP) | ............................. 2001-025033 |
| Feb. 5, 2001 | (JP) | ............................. 2001-027738 |
| Feb. 5, 2001 | (JP) | ............................. 2001-027788 |

(51) Int. Cl.
  *A61B 3/16* (2006.01)
(52) U.S. Cl. ..................................... 600/401
(58) Field of Classification Search ............... 600/401, 600/405, 399, 400, 404

See application file for complete search history.

(56) References Cited

U.S. PATENT DOCUMENTS

| 3,572,100 | A | * | 3/1971 | Grolman et al. ............ 600/401 |
| 5,042,483 | A | | 8/1991 | Nishio |
| 5,092,334 | A | * | 3/1992 | Nishio et al. ............... 600/401 |
| 5,502,521 | A | | 3/1996 | Katou |

FOREIGN PATENT DOCUMENTS

| JP | A 63-135129 | 6/1988 |
| JP | A 64-8947 | 1/1989 |
| JP | A 64-8948 | 1/1989 |
| JP | A 1-268540 | 10/1989 |
| JP | A 7-23907 | 1/1995 |

* cited by examiner

*Primary Examiner*—Max F. Hindenburg
*Assistant Examiner*—Brian Szmal
(74) *Attorney, Agent, or Firm*—Oliff & Berridge, PLC

(57) ABSTRACT

A non-contact type tonometer includes a fluid blowing device which blows fluid against a cornea of an eye of an examinee; an intraocular pressure measurement part which detects a deformed state of the cornea caused by the blown fluid and determines intraocular pressure of the examinee's eye based on a result of detection of the deformed state; a pulsation detection part which detects pulsation of the examinee; a measurement timing determination part which can determine a measurement timing based on the detected pulsation to obtain a predetermined number of results of measurement on the intraocular pressure in synchronization with different phase points in the pulsation; a command signal input part which inputs a command signal for execution of the measurement; and a control part which outputs a control signal for controlling driving of the fluid blowing device based on the determined measurement timing and the input command signal.

10 Claims, 13 Drawing Sheets

NON-CONTACT TYPE TONOMETER

BACKGROUND OF THE INVENTION

1. Field of the Invention

The present invention relates to a non-contact type tonometer for measuring intraocular pressure of an examinee's eye by blowing compressed air (fluid) to deform a cornea of the eye and detecting a deformed state thereof.

2. Description of Related Art

Intraocular pressure changes with time in synchronization with pulsation (pulse wave) of blood. When the intraocular pressure is measured at random in time by a non-contact type tonometer, it is uncertain which point in variations in intraocular pressure is being measured. For example, if the number of times that measurement is executed is small, the lowest value in the variations in intraocular pressure may be measured even though the actual intraocular pressure is high. In the case of screening such as a mass examination, intraocular hypertension may be overlooked. For this reason, there has been proposed a non-contact type tonometer which measures intraocular pressure in the timing synchronized with a predetermined phase point (position) in pulsation while detecting the pulsation.

As to which value in the variations in intraocular pressure is measured, in general, it depends on purposes of diagnosis, etc. When a contact-applanation-type tonometer is used for making evaluations of measurement results, it requires an average value of measurement results obtained at plural different points in the pulsation phase in addition to a measurement result at an arbitrary point in the pulsation phase. The conventional non-contact type tonometer, however, could provide only the measurement result corresponding to the arbitrary point in the pulsation phase.

It is said that such detection of the pulsation is preferably executed with respect to the forehead of an examinee because the pulsation in the forehead has the periods close to the periods of the intraocular pressure variations. When the pulsation is detected in the forehead, however, there may occur changes due to blinking or otter reasons and reflective movements of the examinee's body by air blow. This results in difficulty in accurately detecting the pulsations Moreover, there are some examinees whose pulse rate and blood pressure change as the measurement is started. This makes it more difficult to perform measurement of accurate intraocular pressure.

SUMMARY OF THE INVENTION

The present invention has been made in view of the above circumstances and has an object to overcome the above problems and to provide a non-contact type tonometer capable of appropriately, efficiently perform measurement of intraocular pressure based on pulsation.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a non-contact type tonometer including: fluid blowing means which blows fluid against a cornea of an eye of an examinee; intraocular pressure measurement means which detects a deformed state of the cornea caused by the blown fluid and determines intraocular pressure of the examinee's eye based on a result of detection of the deformed state; pulsation detection means which detects pulsation of the examinee; measurement timing determination means which can determine a measurement timing based on the detected pulsation to obtain a predetermined number of results of measurement on the intraocular pressure in synchronization with different phase points in the pulsation; command signal input means which inputs a command signal for execution of the measurement; and control means which outputs a control signal for controlling driving of the fluid blowing means based on the determined measurement timing and the input command signal.

According to another aspect of the present invention, there is provided a non-contact type tonometer including: fluid blowing means which blows fluid against a cornea of an eye of an examinee; intraocular pressure measurement means which detects a deformed state of the cornea caused by the blown fluid and determines intraocular pressure of the examinee's eye based on a result of detection of the deformed state; pulsation detection means which detects pulsation of the examinee; measurement timing determination means which determines a measurement timing to obtain a predetermined number of results of measurement on the intraocular pressure in synchronization with an intended phase point in the pulsation, the determination means determining a measurement timing based on a pulsation previously detected and sampled; command signal input means which inputs a command signal for execution of the measurement; and control means which outputs a control signal for controlling driving of the fluid blowing means based on the determined measurement timing and the input command signal.

Furthermore, according to another aspect of the present invention, there is provided a non-contact type tonometer including: fluid blowing means which blows fluid against a cornea of an eye of an examinee; intraocular pressure measurement means which detects a deformed state of the cornea caused by the blown fluid and determines intraocular pressure of the examinee's eye based on a result of detection of the deformed state; first pulsation detection means which detects pulsation in a first position near an eyeball of the examinee; second pulsation detection means which detects pulsation in a second position different from the first position; pulsation phase shift detection means which obtains a phase shift between the pulsations detected by the first and second pulsation detection means respectively; measurement timing determination means which determines a measurement timing based on the obtained pulsation phase shift and a detection result by the second pulsation detection means; command signal input means which inputs a command signal for execution of measurement; and control means which outputs a control signal for controlling driving of the fluid blowing means based on the determined measurement timing and the input command signal.

According to another aspect of the present invention, there is provided a non-contact type tonometer including; fluid blowing means which blows fluid against a cornea of an eye of an examinee; intraocular pressure measurement means which detects a deformed state of the cornea caused by the blown fluid and determines intraocular pressure based on a result of detection of the deformed state; first pulsation detection means which detects pulsation in a first position near an eyeball of the examinee; second pulsation detection means which detects pulsation in a second position different from the first position; measurement timing determination means which determines a measurement timing based on the previously detected pulsation by the first pulsation detection means so that the intraocular pressure measurement is executed in synchronization with an intended phase point in the previously detected pulsation, and information means which informs that a period of the pulsation detected by the second pulsation detection means after determination of the measurement timing has changed.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of a preferred embodiment of a non-contact type tonometer embodying the present invention will now be given referring to the accompanying drawings.

Figure 1:
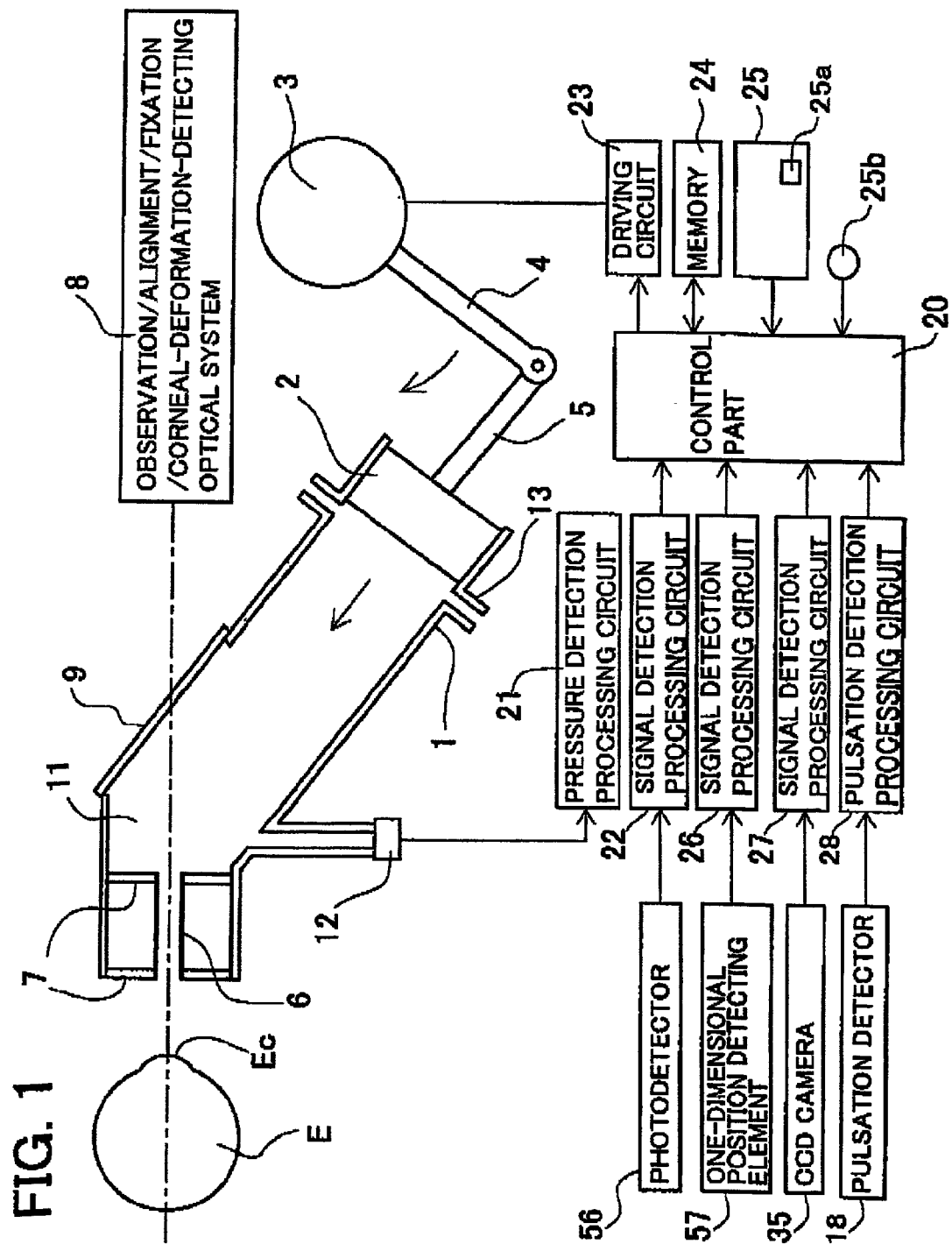
FIG. 1 is schematic structural view of an air blowing mechanism of a non-contact type tonometer viewed from side and a schematic block diagram of a control system of the tonometer in a first embodiment according to the present invention.
Figure 2:
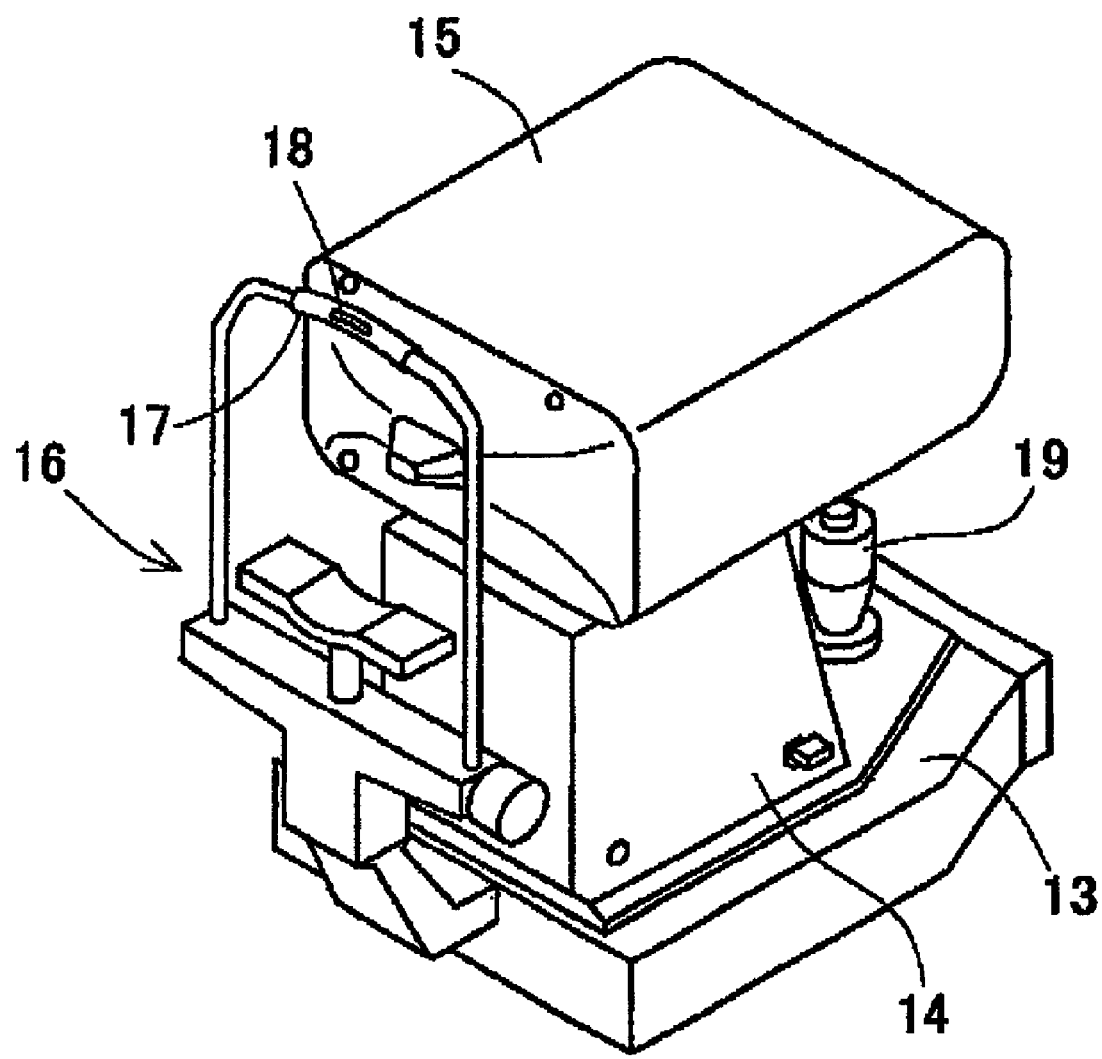
FIG. 2 is a perspective view of the tonometer of FIG. 1.

FIG. 1 is a schematic structural view of an air (fluid) blowing mechanism of the non-contact type tonometer viewed from side and a schematic block diagram of a control system of in a first embodiment. FIG. 2 is a perspective view of the tonometer of FIG. 1.

Numeral 1 is a cylinder for air compression, which is arranged inclined to a horizontal line of a main unit of the tonometer. Numeral 2 is a piston and numeral 3 is a rotary solenoid. When this rotary solenoid 3 is supplied with electric charge (electric current, voltage) as driving energy, the piston 2 is pushed up in the cylinder 1 by means of an arm 4 and a connecting rod 5. Air in an air compression chamber 11 communicating with the cylinder 1 is compressed with a rise of the piston 2. The compressed air is then blown through a nozzle 6 against a cornea Ec of an examinee's eye E. The rotary solenoid 3 is provided with an unillustrated coil spring. When supply of electric charge as driving energy is stopped, the piston 2 is moved down by an urging force of the coil spring in a downward direction and is returned to an initial position.

Numeral 7 is a transparent glass plate which holds the nozzle 6 and allows light from an optical system 8 mentioned later to pass therethrough. The glass plate 7 also serves as a side wall of the air compression chamber 11. Numeral 9 is a transparent glass plate disposed at the back of the nozzle 6. This glass plate 9 constitutes a back wall of the chamber 11 and allows the light from the optical system 8 to pass therethrough. The optical system 8 is disposed behind the glass plate 9. Numeral 12 is a pressure sensor which detects the pressure in the air compression chamber 11.

Numeral 20 is a control part. The following components are connected to this control part 20: a pressure detection processing circuit 21 for the pressure sensor 12; a signal detection processing circuit 22 for a photodetector 56 of a corneal deformation detection optical system; a signal detection processing circuit 26 for a one-dimensional position detecting element 57 used for detection of a working distance; a signal detection processing circuit 27 for a CCD camera 35; a pulsation detection processing circuit 28 for a pulsation detector 18; a driving circuit 23 for driving the rotary solenoid 3; a memory 24 for storing measurement data, control conditions of measurement, etc. Numeral 25 is an input part which is provided with a switch 25a for selecting a measurement mode and others. Numeral 25b is a measurement start switch.

The pulsation detector 18 for detecting pulsation of an examinee is attached to a forehead rest 17 provided in a head support unit 16 for supporting the head (face) of the examinee, as shown in FIG. 2. In the present embodiment, the pulsation detector 18 is provided in the forehead rest 17 in order to obtain substantially the same phase as the phase of pulsation in the eyeball. Alternatively, the pulsation detector 18 may be disposed in another position in contact with the examinee's face, for example, in a chinrest. It is also possible to detect the pulsation in a portion other than the examinee's face. The pulsation detector 18 also serves as a judgement function to judge whether the examinee's face is in stable contact with the forehead rest 17.

The pulsation detector 18 is constructed of a light emitting part and a light receiving part. The light emitting part is a light emitting diode (LED) which emits light having a narrow Ad wavelength band in a near-infrared region corresponding to the HE absorption spectrum of hemoglobin in the blood. The light receiving part is a photodiode. The blood-hemoglobin has a strong absorption spectrum with respect to light in a predetermined wavelength band. The intensity of reflection light from a living body irradiated by the light in this wavelength band varies according to the quantity of hemoglobin which changes with a change in volume of a blood-vessel. Accordingly, this intensity of reflection light is converted to an electric signal, so that the pulsation can be detected. It is to be noted that the blood-hemoglobin has a wide absorption spectrum with respect to a visible wavelength region as well as the near-infrared wavelength region. Therefore, the light emitting part may be constructed of a white LED or the like. In this case, the light receiving part is desired to have sensitivity to light in a wide wavelength band. For example, a photoconductive element (cell) is used.

In FIG. 2, numeral 15 is a measurement unit which is internally provided with the air blowing mechanism and the optical system 8 mentioned later. This measurement unit 15 is mounted on a movable carriage 14 which is horizontally moved on a fixed base 13. This horizontal movement of the movable carriage 14 is carried out by operation of a joystick 19. By operation of a rotary knob of the joystick 19, the measurement unit 15 is moved vertically with respect to the movable carriage 14.

Figure 3:
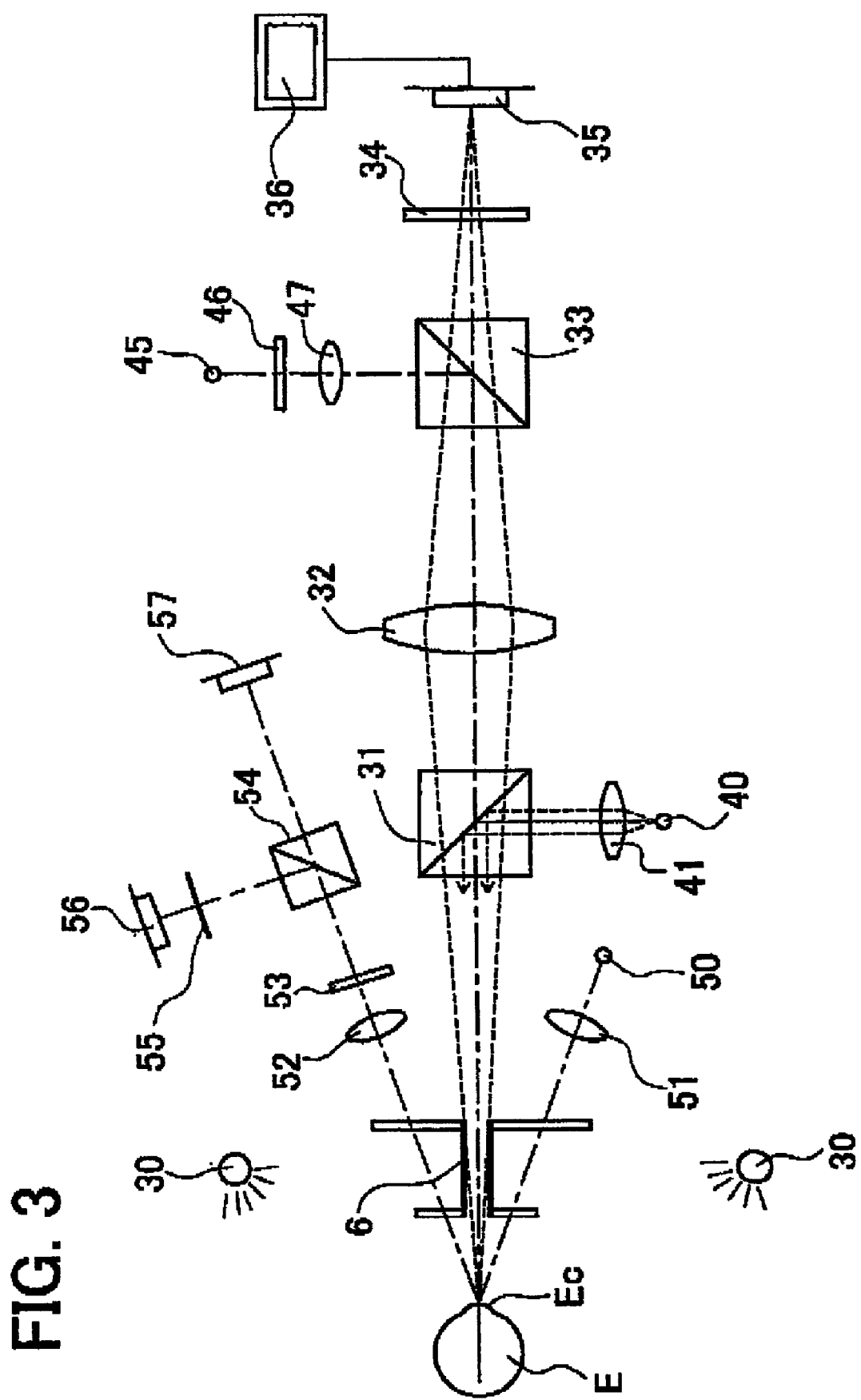
FIG. 3 is a schematic structural view of an optical system, viewed from above, disposed near the back of a nozzle of the air blowing mechanism.

FIG. 3 is a schematic structural view of the optical system 8, viewed from above, disposed behind the nozzle 6. An image of the eye E illuminated by light from an infrared illumination light source 30 is formed on a CCD camera 35 via a beam splitter 31, an objective lens 32, a beam splitter 33, and a filter 34 in turn. The filter 34 has the property of allowing light of each of the light source 30 and a light source 40 for alignment to pass therethrough and of not allowing light of a light source 50 for corneal deformation detection, which will be mentioned later, to pass therethrough. The image of the eye E formed on the camera 35 is displayed on a monitor 36. This allows an examiner to observe the eye E.

The infrared light from the alignment light source (infrared LED) 40 passes through a projection lens 41 and is reflected by the beam splitter 31 to be projected to the cornea Ec from the front. A corneal luminescent spot (index image) formed on the top of the cornea Ec by projection is formed on the camera 35 via the beam splitter 31, the objective lens 32, the beam splitter 33, and the filter 34, This image is used for detection of an alignment state in a vertical and a horizontal directions.

Visible light from a fixation target 46 illuminated by light of a fixation target projecting light source (visible LED) 45 passes through a projection lens 47 and is reflected by the beam splitter 33, and the light passes through the objective lens 32 and the beam splitter 31 toward the eye E. Thus, the examinee (the eye E) can view the fixation target 46 . The examiner instructs the examinee to fix his eye on the fixation target 46 and performs measurement.

Light from the corneal deformation detection light source (infrared LED) 50 is made into substantially parallel luminous flux through a collimator lens 51 and is projected to the cornea Ec. The light reflected by the cornea Ec passes through a light receiving lens 52 and a filter 53 and is reflected by a beam splitter 54. The light is then received by a photodetector 56 via a pin-hole plate 55. The filter 53 has the property of allowing light of the light source 50 to pass therethrough and of not allowing light of each of the light sources 30 and 40 to pass therethrough. This corneal deformation detecting optical system is arranged so that the received light quantity by the photodetector 56 becomes the maximum when the cornea Ec is deformed into a predetermined deformed state (an applanation state).

This corneal deformation detecting optical system also serves as part of a working distance detecting optical system, whereby the light from the light source 50 forms a virtual image of the light source 50 as an index image on the cornea EC The light of this index image passes through the light receiving lens 52, the filter 53, and the beam splitter 54, and is made incident to the one-dimensional position detecting element 57 such as a PSD, a line sensor, or the like. When the eye E (the cornea Ec) is moved in the working distance, the incident position of the light of the index image by the light source 50 is moved on the position detecting element 57. Consequently, the control part 20 can obtain information on the working distance based on an output signal of the position detecting element 57.

Next, the operation of the non-contact type tonometer having the above structure will be explained.

Figure 4:
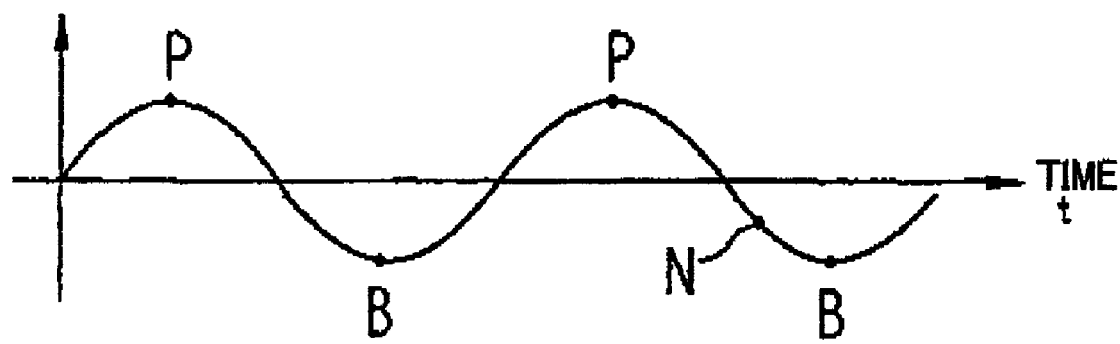
FIG. 4 is an explanatory view showing a peak point, a bottom point, and an arbitrary point in a pulsation phase.

The examiner selects first a measurement mode with the switch 25a to determine at which phase point in a pulsation period the measurement is executed correspondingly. For this measurement mode, as shown in FIG. 4, the following four modes are prepared: a first mode of measuring intraocular pressure in correspondence with peak point P in the pulsation phase; a second mode of measuring in correspondence with bottom point B in the pulsation phase; a third mode of measuring in correspondence with an arbitrary point N in the pulsation phase; and a fourth mode of measuring a predetermined number of times in correspondence with the peak point P and the bottom point B respectively (for example, two times each). The arbitrary point N can be set with a switch on the input part 25 in such a way to determine what percentage of the height of amplitude or what percentage of one period. In the mode of measuring a predetermined number of times in correspondence with the peak point P and the bottom point B respectively, an average value is automatically calculated from the value measured in correspondence with each point. This average value is effective for evaluations of values measured by a Goldmann tonometer of a contact-applanation type.

Figure 5:
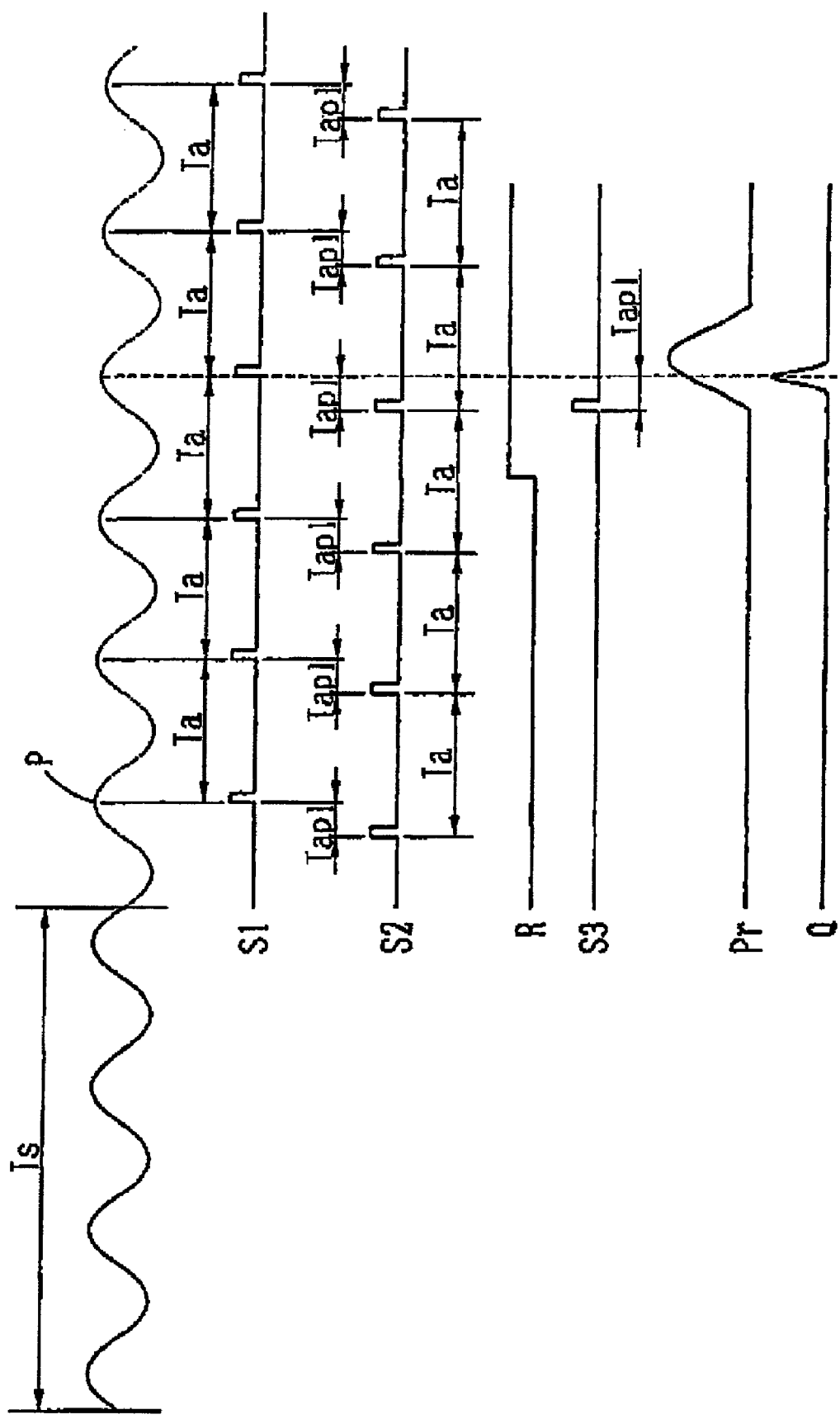
FIG. 5 is an explanatory view showing pulsation and a Age measurement timing for intraocular pressure.

Subsequently, the examiner instructs the examinee to put his forehead into contact with the forehead rest 17. The pulsation of the examinee is thus detected by the pulsation detector 18 attached to the forehead rest 17. The pulsation detector 18 transmits the pulsation of the examinee in the form of an electric signal to the pulsation detection processing circuit 28. A pulsation waveform signal detected by this circuit 28 is input to the control part 20. The control part 20 samples the pulsation waveform signal for a preset sampling time Ts as shown in FIG. 5. This sampling time Ts is set to acquire a pulsation waveform signal for a predetermined time (for example, five seconds) or for a predetermined number of pulsation periods (even one period is sufficient, and three or more periods are more preferable). During this sampling time Ts, the examinee is requested to keep still in order to obtain a stable pulsation waveform signal. Obtaining the stable pulsation waveform signal, the control part 20 determines, from the sampling data, a phase and a period of a subsequent pulsation. The phase and period of the pulsation is preferably determined by average of pulsation waveforms stably sampled. Thereafter, the control part 20 determines a periodic timing of measuring intraocular pressure.

If the pulsation can not be detected by the pulsation detector 18, it is found that the forehead of the examinee is in insufficient contact with the forehead rest 17 and the fixing state of the face is unstable. At this time, the monitor 36 may be controlled to display a message to the effect that the face is not supported stably in order to inform thereof the examiner. The message also may be informed by voice sound.

FIG. 5 shows an example of a mode of examining intraocular pressure in correspondence with the peak point P in the pulsation phase. S1 is a timing of the peak point P in the pulsation phase which is expected after the sampling time Ts. S2 is a timing of execution of intraocular pressure measurement to output a signal S3 for driving the solenoid 3. This measurement timing S2 is determined as a timing shifted back from the timing S1 by an applanation detection time Tap1 required from output of the solenoid driving signal S3 to applanation of the cornea Ec by the blowing of compressed air (namely, until an applanation signal Q outputted from the photodetector 56 becomes peak). The measurement timing S2 is repeated at intervals of a pulsation period Ta.

The applanation detection time Tap1 is explained below. The time needed from the output of the solenoid driving signal S3 until the applanation signal Q becomes peak varies according to the intraocular pressure of the examinee's eye and the rising edge of blowing pressure of the compressed air. The rising edge of blowing pressure after output of the solenoid driving signal S3 can be obtained in advance. Accordingly, if an intraocular pressure value of the examinee'S eye can be predicted, the applanation detection time Tap1 can also be estimated. In the case where second and subsequent measurements are performed with respect to the same examinee's eye, in each measurement, the intraocular pressure value obtained in the preceding measurement is set as a predicted value and the applanation detection time Tap1 then calculated by the control part 20 is used in the next following measurement. In this way, in each of the second and subsequent measurements, the applanation detection time Tap1 determined in the immediately preceding measurement (or the earlier measurement) is used to determine the measurement timing S2. Thus, the peak of the pulsation waveform and the peak of the applanation signal Q will easily coincide. In the first measurement, the applanation detection time Tap1 is set with the use of an average intraocular pressure value. In addition, if the intraocular pressure of the examinee's eye can be predicted to some extent, the corresponding intraocular pressure value may be input through the input part 25 to set the applanation detection time Tap1.

After determination of the measurement timing S2 from the sampling data on the pulsation, the control part 20 causes the monitor 36 to display to that effect and puts the apparatus into an intraocular pressure measurement enabled state. The examiner manipulates the joystick 19 in accordance with the alignment information displayed on the monitor 36 to move the measurement unit 15 for alignment. The alignment in the vertical and horizontal directions is made so that the index image (i.e. the corneal luminescent spot) formed by the light of the light source 40 is brought in a predetermined relation with an unillustrated reticule displayed on the monitor 36. The alignment in the working distance direction is performed in accordance with a working distance mark displayed on the monitor 36 based on the working distance information provided from the position detecting element 57. The details of this alignment is referred to U.S. Pat. No. 5,502,521 corresponding to Japanese Patent Unexamined Publication No. 7-23907 filed by the same applicant as that of the present invention. Alternatively, the alignment may be conducted by automatically moving the measurement unit 15 based on the detection information on those alignment index images.

The control part 20 obtains an alignment completion signal R when the index image by the light source 40, detected by the camera 35, and the index image by the light source 50, detected by the position detecting element 57, come in a predetermined acceptable range, respectively. Upon receipt of the alignment completion signal R, which acts as a command signal for execution of measurement, the control part 20 outputs the solenoid driving signal 3 in synchronization with the measurement timing S2 immediately after the command signal. That is, the control part 20 causes the driving circuit 23 to supply electric charge as driving energy to the rotary solenoid 3. The rotary solenoid 3 is thus actuated. It is to be noted that in the case where measurement is manually carried out without use of the alignment completion signal R, the control part 20 outputs the solenoid driving signal 3 in synchronization with the measurement timing S2 immediately after a trigger signal from the switch 25b is input.

The actuated rotary solenoid 3 causes the piston 2 to rise, compressing the air in the air compression chamber 11, then blowing the compressed air from the nozzle 6 against the cornea Ec. The cornea Ec is gradually deformed by the compressed air blown thereto. When the cornea Ec comes into a flat state, the quantity of incident light to the photodetector 56 becomes the maximum. The output signal from the photodetector 56 and the output signal from the pressure sensor 12 are sequentially processed and input to the control part 20. With reference to the time when the applanation signal Q outputted from the photodetector 56 shows a peak, the control part 20 calculates an average value of pressure Pr obtained in a predetermined time width including times before and after the peak, thereby determining an intraocular pressure value.

In second and subsequent measurements which are sequentially performed, output of the solenoid driving signal S3 is allowed after a lapse of both the time needed for charging electric charge to drive the solenoid 3 and the time for taking air in the cylinder 1.

As mentioned above, the step of detecting pulsation and the step of measuring intraocular pressure are separated and, based on the pulsation previously detected in a still state of the examinee, the periodic measurement timing corresponding to the subsequent pulsation of the examinee is determined. Even if the pulsation can not be detected because the examinee blinks during measurement or reflexively moves his body during repetitive measurements, accordingly, the intraocular pressure measurement at an intended pulsation phase point can be smoothly executed. To be more specific, the measurement timing corresponding to any pulsation of the examinee indicated by a dotted line in FIG. 5 is determined based on the sampling of previous pulsation (for example, which occurred earlier than the immediately preceding pulsation). Thus, even if the pulsation of the examinee indicated by the dotted line can not be detected, the measurement timing corresponding to the undetected pulsation can be determined.

Figure 6:
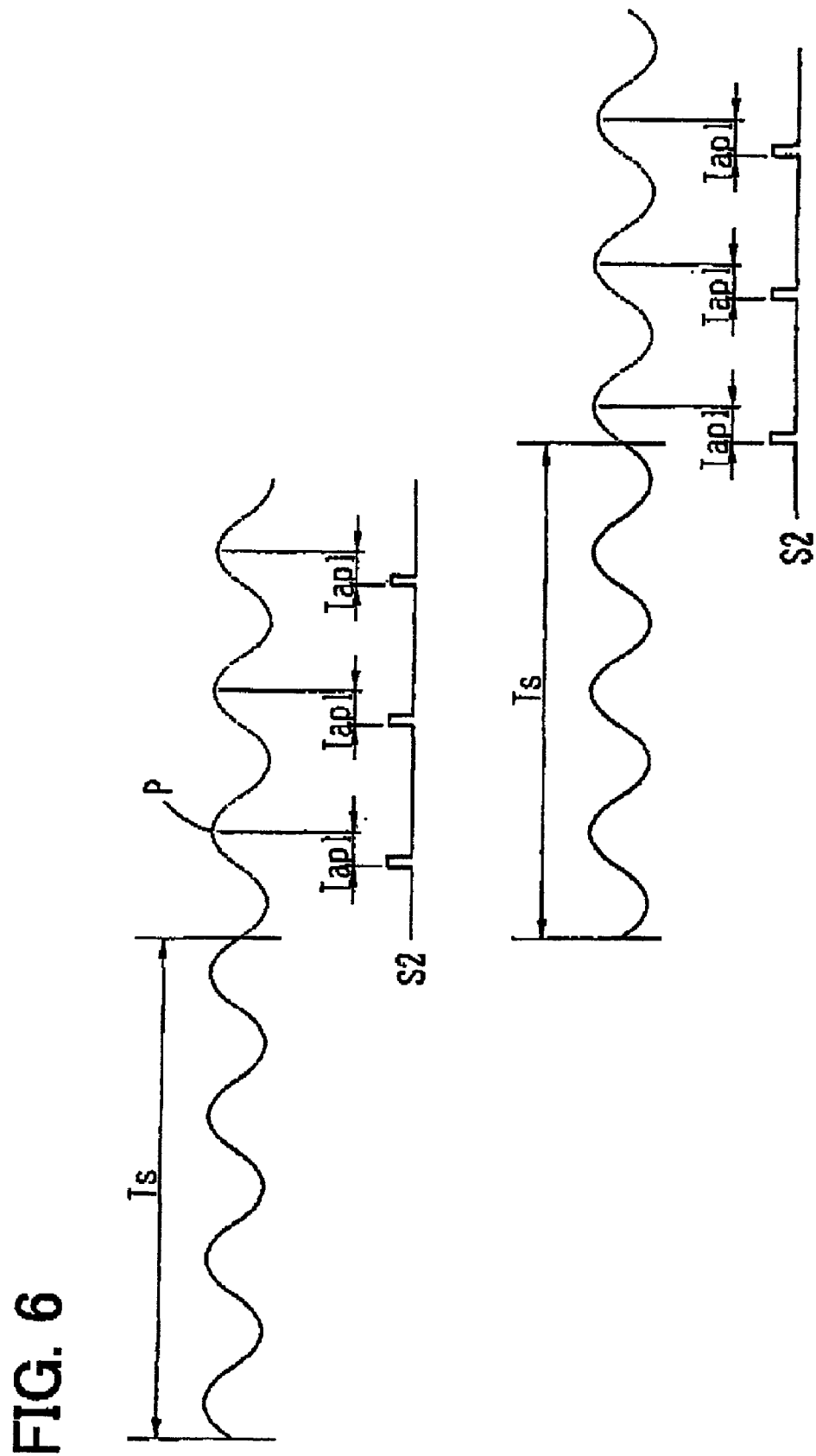
FIG. 6 is an explanatory view showing a timing chart in the case of sequentially determining another measurement timing in relation to a sampling time.

The measurement timing S2 is normally determined as above. It is more preferable to successively sample pulsation and sequentially renew the measurement timing S2. When no pulsation can be detected during sampling, the measurement timing S2 is determined based on the pulsation detected in the previous sampling. For example, as shown in FIG. 6, samplings are repeated at intervals of a sampling time of 5 seconds and the measurement timing S2 is determined in each sampling. When pulsation is not stably obtained during current sampling, the preceding determined measurement timing S2 is used as it is.

Figure 7:
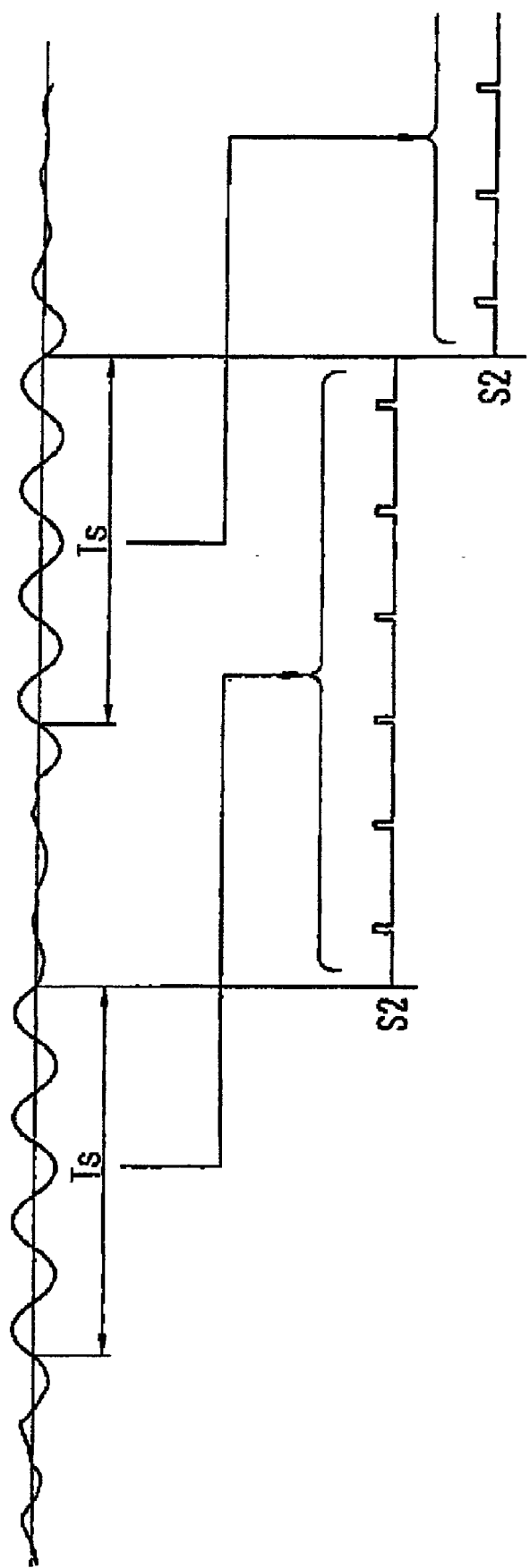
FIG. 7 is an explanatory view showing a timing chart in the case of sequentially determining another measurement timing in relation to a sampling time with satisfactory waveforms.

As shown in FIG. 7, it may be arranged to renew the measurement timing S2 at the time when an appropriate waveform is acquired during continuous sampling. Also in this case, the previously determined measurement timing S2 can be used even when pulsation can not be detected during sampling. This makes it possible to smoothly perform measurement. When the appropriate waveform is obtained, the measurement timing S2 is sequentially renewed. This can reduce synchronization shift of the pulsation which may occur in association with a lapse of time. As a result of this, the accuracy can be enhanced.

The above matter shows that, if the sampling time Ts is set to one period of the pulsation, the measurement timing S2 is determined based on the period and phase of the pulsation whenever one pulsation waveform is detected. When no pulsation can be detected, on the other hand, the preceding measurement timing S2 is periodically repeated. To be more specific, based on the pulsation previously detected in a still state of the examinee, a periodic measurement timing S2 (for example, two or more timings) corresponding to the pulsation of the examinee which occurs after the previously detected pulsation is determined.

Next, explanation is made on the case where the mode of measuring a predetermined number of times in correspondence with the peak point P and the bottom point B in the pulsation phase respectively. In this mode, with respect to the same examinee's eye, the intraocular pressure thereof is automatically measured two times each in correspondence with the peak point and the bottom point in the pulsation phase.

Figure 8:
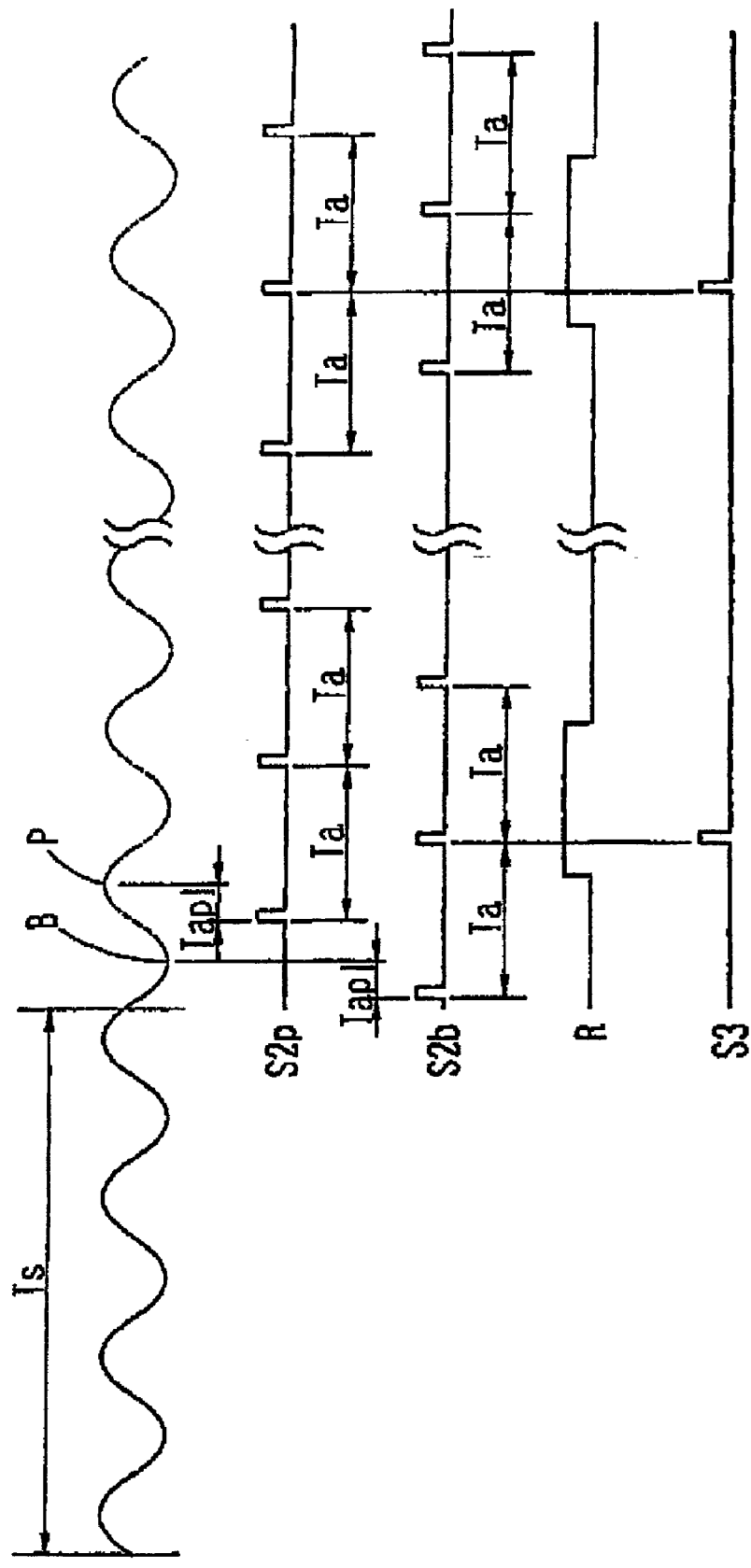
FIG. 8 is an explanatory view showing a timing chart in the case of repeatedly measuring intraocular pressure in the timing corresponding to a peak point and a bottom point in the pulsation phase.

As shown in FIG. 8, the control part 20 determines the phase and the period of the pulsation from the sampling data and calculates a measurement timing s2p corresponding to the peak point P in the pulsation phase and a measurement timing S2b corresponding to the bottom point B in the pulsation phase so that each timing is shifted back from each point by the applanation detection time Tap1 in the same manner as mentioned above. The two measurement timings (timing patterns) S2p and S2b are determined respectively, sequentially in correspondence with the period of pulsation.

Upon receipt of the alignment completion signal R after the sampling of pulsation, the control part 20 outputs the solenoid driving signal S3 in synchronization with either earlier one of the subsequent measurement timings S2p and S2b. In FIG. 8, after receipt of the alignment completion signal R, the measurement timing S2b corresponding to the bottom point B comes first, and then the measurement timing s2p corresponding to the peak point P comes. In this case, the measurement timing S2b is earlier than the other timing S2p and therefore a first measurement result corresponds to the bottom point B. Afterward, the measurement in the measurement timing S2p corresponding to the peak point P can not be performed immediately after the previous measurement relative to the bottom point B. This is because the charging time for charging electric charge for driving the solenoid 3 and the intake time for taking air in the cylinder 1 are needed. After the blowing of the compressed air is allowed, the alignment completion signal R is obtained again. Then, if the measurement timing S2p comes earlier, the solenoid driving signal S3 is outputted in synchronization with this timing. This measurement result corresponds to the peak point P.

In the above manner, the control part 20 controls the order of measurement so that the measurement is executed in synchronization with the measurement timing S2p or S2b, whichever is earlier, and two measurement results are obtained in correspondence with each point. If two results at the peak point P are obtained first in relation to an input timing of the alignment completion signal R, then the order of measurement is controlled to obtain two results at the bottom point B. When the measurement is performed two times each in correspondence with the peak point P and the bottom point B, an average value thereof is automatically calculated.

Figure 9:
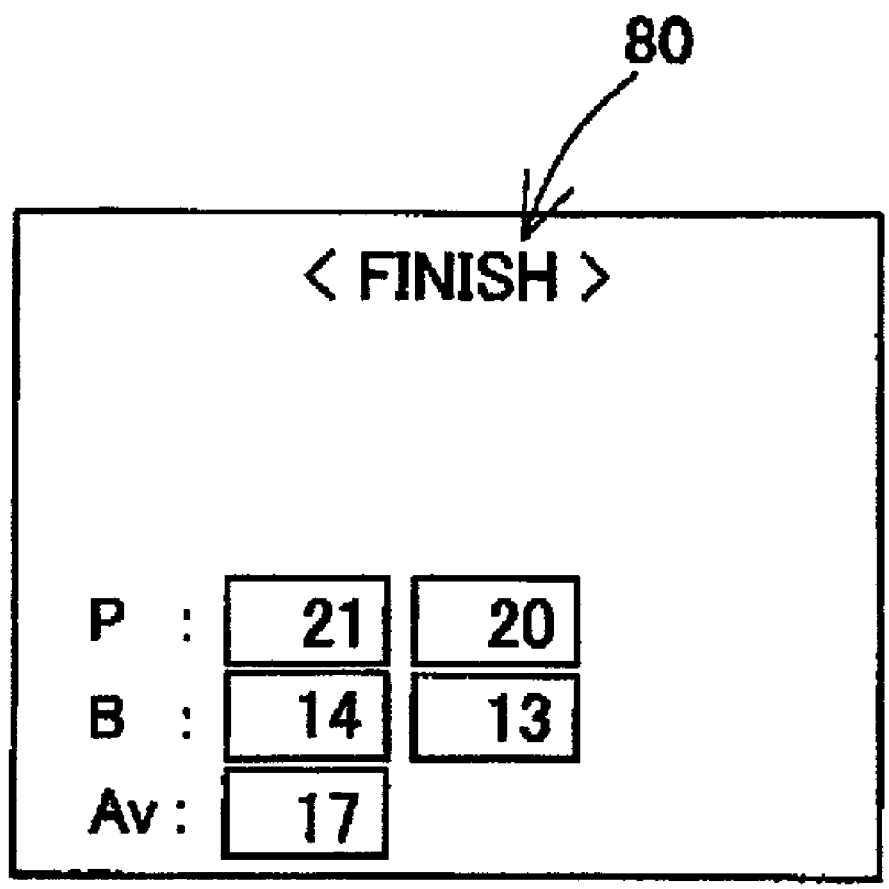
FIG. 9 is an explanatory view showing an example of a display screen for displaying measurement results.

The measurement results are displayed on the monitor 36 whenever the measurement is executed. In addition, when respective two results are obtained, a message informing the completion of measurement is displayed on the monitor 36. FIG. 9 shows an example of a display screen of the monitor 36 in this stage. Numeral 80 is the message indicating the measurement completion. In the screen below the message 80, the measurement results are individually displayed. In the example shown in FIG. 9, the measurement results corresponding to the peak point P in the pulsation phase are displayed on the right of an indication "P" on the screen and the measurement results corresponding to the bottom point B are displayed on the right of an indication "B". On the right of an indication "Av" on the screen, an average value determined by calculation is displayed. In the case where the results are printed out by a printer, similarly, they are outputted in a classified condition to show to which point the result corresponds. A similar manner is applied to the case where the data is outputted in an external computer. In this case, the displayed indications "P" and "B" show in which timing of the previously determined timings the measurement was executed.

Figure 10:
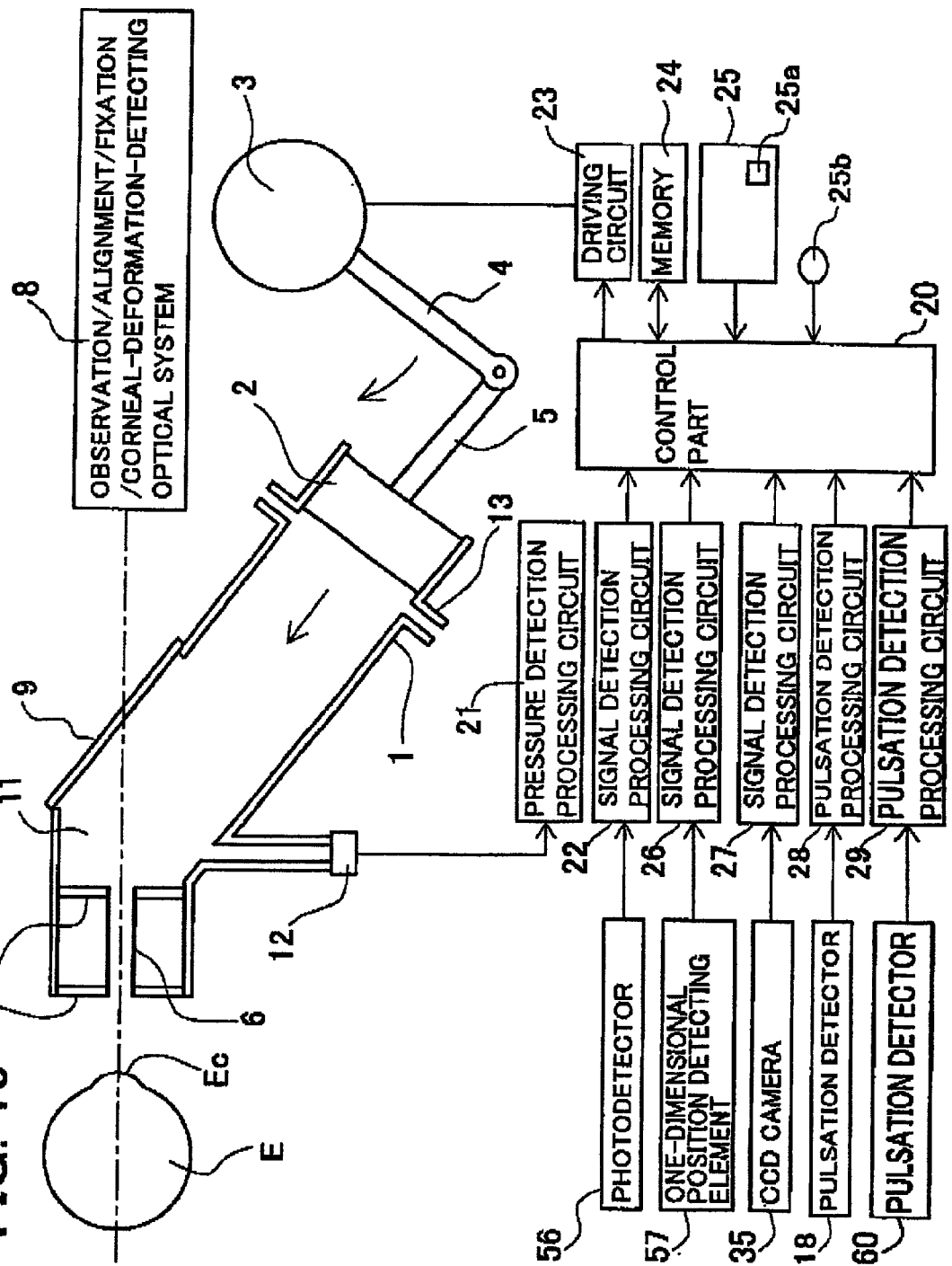
FIG. 10 is a schematic structural view of an air blowing mechanism of a non-contact type tonometer viewed from side and a schematic block diagram of a control system of the tonometer in a second embodiment according to the present invention.
Figure 11:
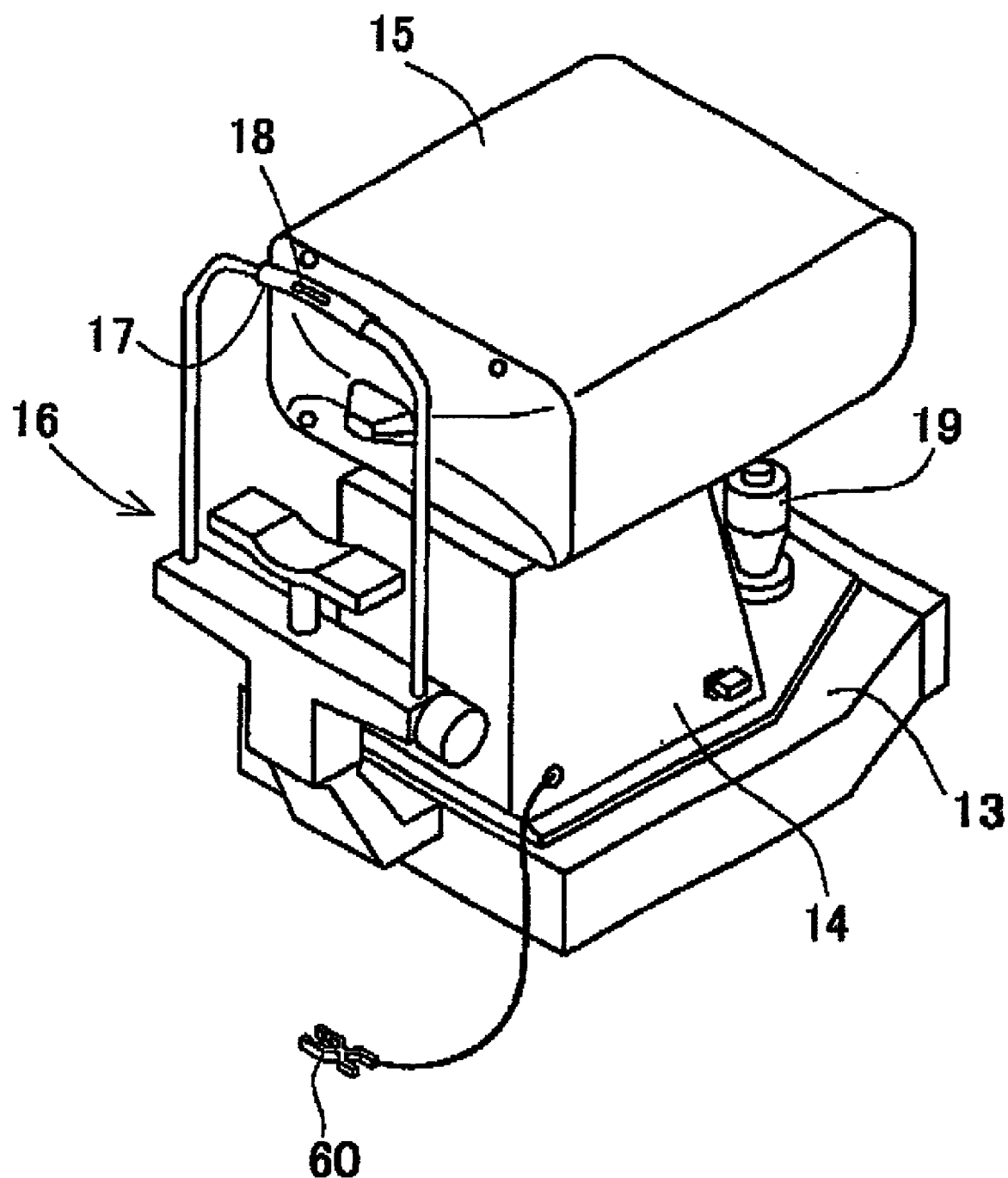
FIG. 11 is a perspective view of the tonometer of FIG. 10.

Next, a second embodiment of the present invention will be explained with reference to the drawings. FIG. 10 is a schematic structural view of an air (fluid) blowing mechanism of a non-contact type tonomneter viewed from side and a schematic block diagram of a control system in the second embodiment. FIG. 11 is a perspective view of the tonometer of FIG. 10. Like elements in this embodiment to those in the first embodiment are given like numerals.

Numeral 60 is a second pulsation detector capable of detecting pulsation of an examinee by pinching the examinee's finger. This detector 60 is attached to an end of a cable provided extending from the movable carriage 14. The detector 60 has the same structure as that of the pulsation detector 18. A pulsation detect ion processing circuit for the pulsation detector 60 is connected to the control part 20.

The operation of the non-contact type tonometer having the above structure will be explained below.

An examiner attaches the pulsation detector 60 to the examinee's finger to detect the pulsation in the finger. The examiner then instructs the examinee to put his forehead into contact with the forehead rest 17 to detect the pulsation in the forehead by the pulsation detector 18. The pulsation detector 18 converts the pulsation into an electric signal and transmits to the pulsation detection processing circuit 28. Similarly, the pulsation detector 60 converts the pulsation into an electric signal and transmits to the pulsation detection processing circuit 29. Each pulsation waveform signal detected by the pulsation detection processing circuits 28 and 29 is input to the control part 20.

Figure 12:
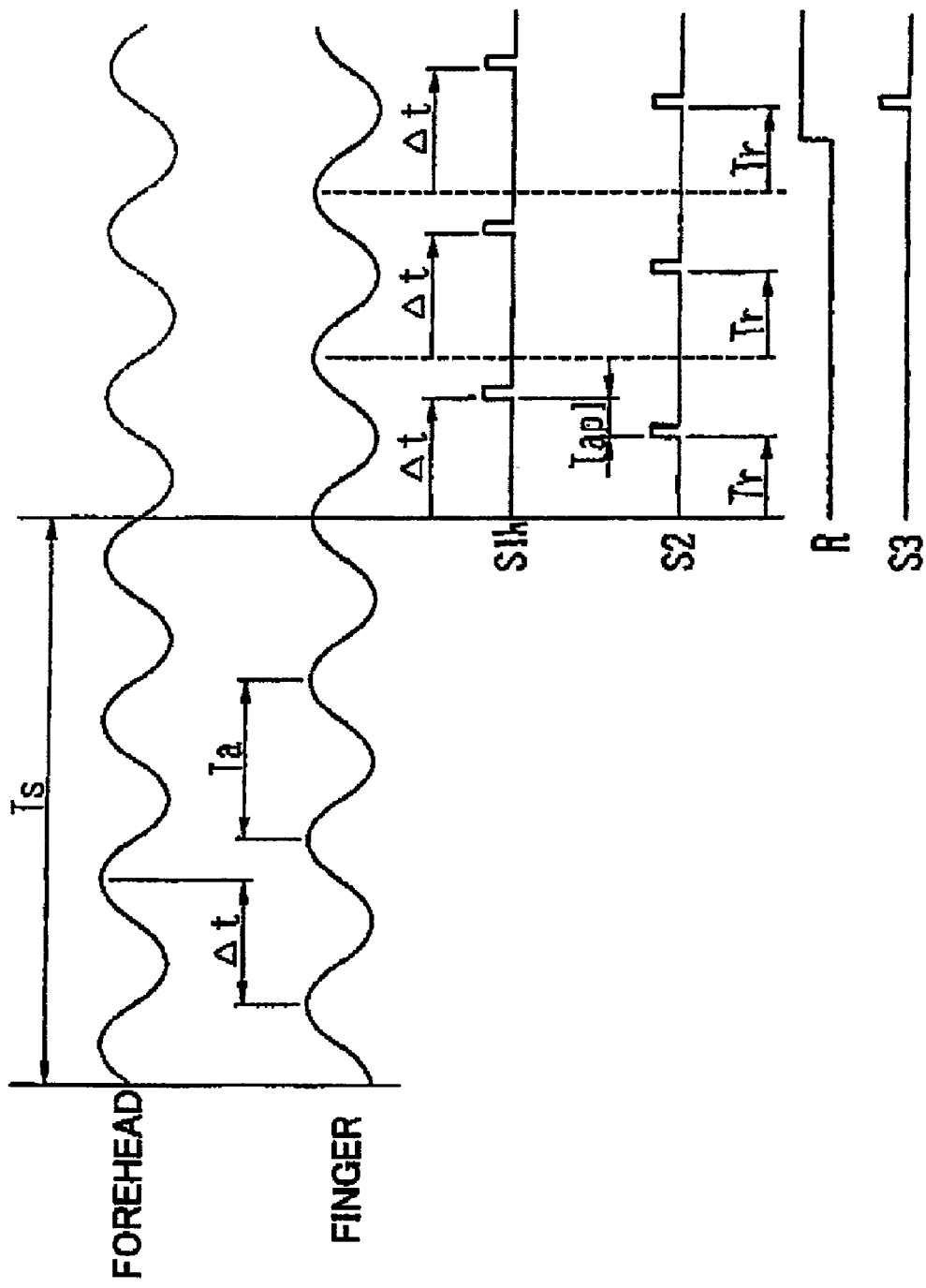
FIG. 12 is an explanatory view showing the pulsation detected in a forehead and that in a finger and the measurement timing for intraocular pressure.

The control part 20 samples the waveform signal representative of pulsation in the forehead for the sampling time Ts, as shown in FIG. 12. On the other hand, the control part 20 successively samples the waveform signal representative of pulsation in the finger.

Based on the sampling data from the pulsation detector 18 and that from the pulsation detector 60, the control part 20 determines a pulsation phase shift (difference) $\Delta t$ therebetween. It is to be noted that the finger is farther than the forehead from the heart and therefore the pulsation phase in the finger tends to lag behind that in the forehead. For this reason, the pulsation phase shift $\Delta t$ is determined as a deviation (difference) between the finger pulsation and the forehead pulsation occurring after one heartbeat. Based on the determined pulsation phase shift $\Delta t$ and the pulsation detected from the finger, the control part 20 determines the timing of intraocular pressure measurement with reference to the pulsation phase points in the forehead. In the present embodiment, explanation is made assuming that the measurement is executed in synchronization with the peak point in the pulsation phase in the forehead.

The control part 20 determines the timing of intraocular pressure measurement in the following manner. In FIG. 12, S1$h$ is a timing of the peak point in the pulsation phase in the forehead. This timing is determined as a timing later than the peak point in the pulsation phase detected in the finger by the pulsation phase shift $\Delta t$. S2 is a timing of intraocular pressure measurement to output the signal S3 for driving the solenoid 3. This measurement timing 52 is determined as a timing shifted back from the timing S1$h$ by the applanation detection time Tap1. In other words, the measurement timing S2 is calculated by the following expression;

Pulsation phase shift $\Delta t$–Applanation detection time Tap1=Measurement timing after time Tr.

The timing S2 thus becomes the measurement timing after a lapse of time Tr from the peak point in the pulsation phase detected in the finger.

When the peak point in the pulsation phase in the finger are detected sequentially by the pulsation detector 60, the control part 20 determines the measurement timing S2 as above. Upon receipt of the alignment completion signal R, which acts as a command signal for execution of measurement, the control part 20 outputs the solenoid driving signal S3 in synchronization with the measurement timing S2 coming immediately after the command signal, thus executing measurement.

In the above described case, the subsequent pulsation periods are unchanged (be in an acceptable range) with respect to the sampling of the pulsation from the forehead. When the pulsation periods change, alternatively, the control part 20 corrects the measurement timing S2 in the following manner.

Figure 13:
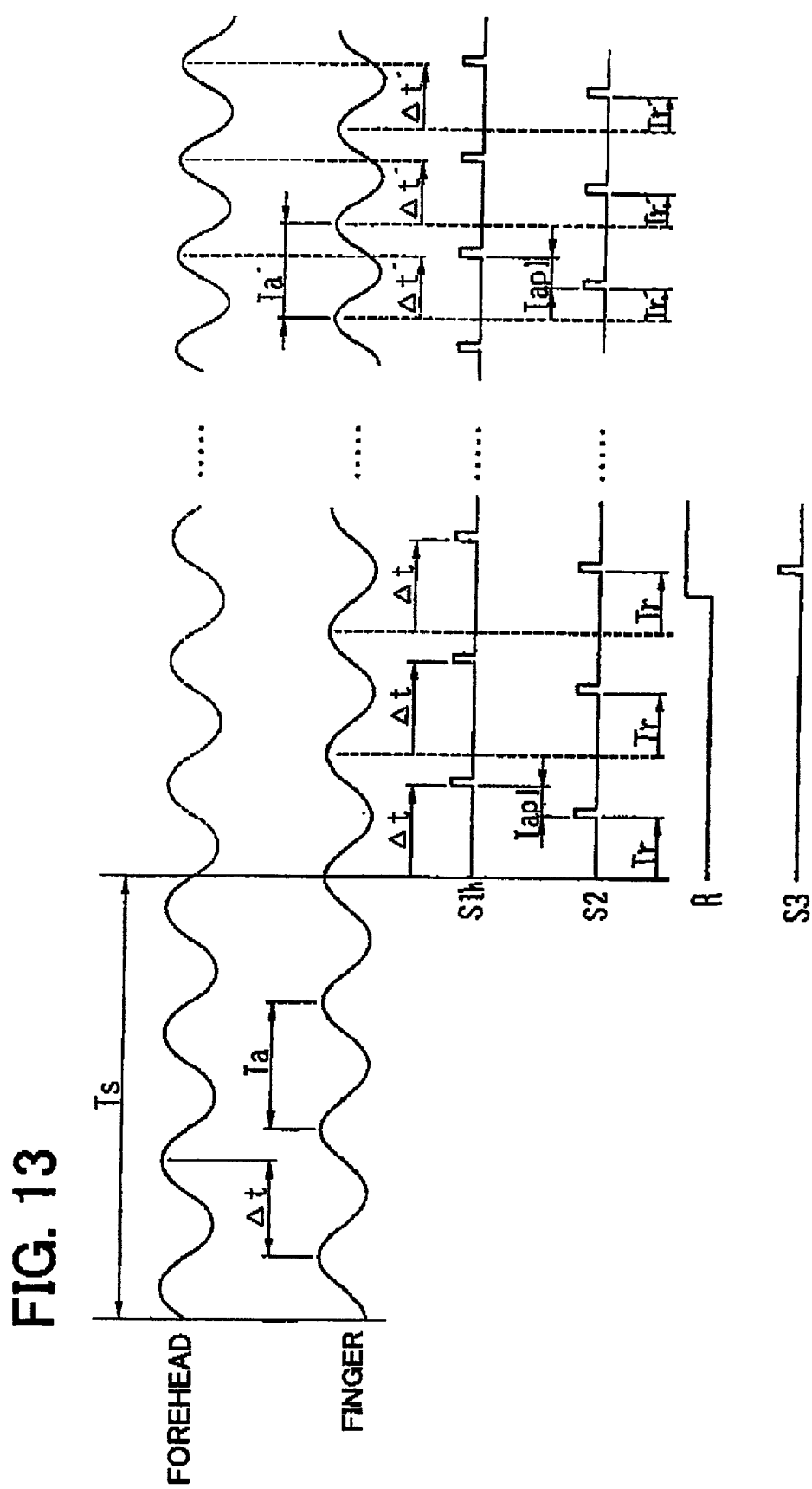
FIG. 13 is an explanatory view showing the measurement timing for intraocular pressure provided in the case where a pulsation period change.

Assuming that the pulsation period Ta in the first detection changes to another period Ta' during measurement as shown in FIG. 13, the pulsation phase shift $\Delta t'$ occurring at this time is obtained by the expression;

$$\Delta t' = Ta' - (Ta - \Delta t)$$

where the traveling rate of a pulse wave is supposed to be constant.

When the pulsation phase shift $\Delta t'$ in the pulsation period Ta' is determined, the measurement timing S2 after correction is calculated by the following expression in the same way as above;

Pulsation phase shift $\Delta t'$–Applanation detection time Tap1=Time Tr'.

It is to be noted that there may be a case where the blood pressure rises as the heart rate increases by normal physiological reaction. It is considered that the rise of the blood pressure also causes velocity of pulse conduction to increase. In such the case, the phase difference becomes shorter. Accordingly, L the measurement timing 62 may be corrected by insertion of a coefficient, for example, (Ta'/Ta), in the above expression In general, it is corrected by any function expressed as follows;

$$\Delta t' = f(Ta, Ta', \Delta t).$$

In the above explanation, when the pulsation period Ta has changed, the measurement timing S2 is determined from the pulsation detection result from the pulsation detector 60. Alternatively, it may be arranged to simply inform that the pulsation period detected by the pulsation detector 60 has changed, without determination of the pulsation phase shift $\Delta t$. This example is explained below.

In this example, at first, the timing of the peak point in the estimated pulsation phase in the finger after the sampling time Ts is determined from the sampling data obtained by the pulsation detector 18. The measurement timing S2 is found, as in the above case, as the timing shifted back from the peak point in the pulsation phase by the applanation detection time Tap1. The measurement timing S2 in this example is determined from the detection result by the pulsation detector 18 and is repeated at intervals of the pulsation period Ta.

The measurement of intraocular pressure is enabled after determination of the measurement timing S2. Upon receipt of the alignment completion signal R, the control part 20 outputs the solenoid driving signal S3 to execute the measurement. In the measurement-enabled state, the pulsation detector 60 monitors changes in pulsation. When the period of pulsation (heart rate) detected by the detector 60 deviates from a predetermined acceptable value, the control part 20 causes the monitor 36 to display to that effect and sounds an unillustrated alarm to inform the examiner. After that, the mode of sampling pulsation from the detector 18 for the time Ts is established again. A new measurement timing S2 is then determined based on the pulsation detected by the detector 18. The measurement of intraocular pressure is thus enabled. If the measurement is executed after the change in the pulsation period Ta is detected, a message that the data obtained by the measurement is lacking in reliability may be displayed along with a measured value.

As explained above, according to the present invention, the measurement of intraocular pressure based on pulsation can be efficiently, appropriately executed.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A non-contact type tonometer including:
    fluid blowing means which blows fluid against a cornea of an eye of an examinee;
    intraocular pressure measurement means which detects a deformed state of the cornea caused by the blown fluid and determines intraocular pressure of the examinee's eye based on a result of detection of the deformed state;
    pulsation detection means which detects pulsation of the examinee;
    measurement timing determination means which can determine a measurement timing based on the detected pulsation;
    command signal input means which inputs a command signal for execution of intraocular pressure measurement;
    control means which outputs a control signal for controlling driving of the fluid blowing means based on the determined measurement timing and the input command signal; and
    mode selection means which includes a first mode and a second mode, the mode selection means selecting one of the first mode for obtaining a measurement value of the intraocular pressure at a measurement timing corresponding to at least one of a peak point in a phase of pulsation, a bottom point in the phase of pulsation and an arbitrary point in the phase of pulsation and the second mode for obtaining a measurement value of the intraocular pressure at a first measurement timing corresponding to the peak point and a measurement value of the intraocular pressure at a second measurement timing corresponding to the bottom point, wherein when the second mode is selected, the measurement timing determination means determines the first measurement timing based on the peak point in the phase of the detected pulsation and the second measurement timing based on the bottom point in the phase of the detected pulsation.

2. The non-contact type tonometer according to claim 1, wherein the intraocular pressure measurement means calculates an average value of the measurement value at the first measurement timing corresponding to the peak point and the measurement value at the second measurement timing corresponding to the bottom point.

3. The non-contact type tonometer according to claim 2 further including output means which outputs the measurement value obtained at the first measurement timing, the measurement value obtained at the second measurement timing, and the average value of those measurement values so that those values are distinguishable.

4. A non-contact type tonometer including:
fluid blowing means which blows fluid against a cornea of an eye of an examinee;
intraocular pressure measurement means which detects a deformed state of the cornea caused by the blown fluid and determines intraocular pressure of the examinee's eye based on a result of detection of the deformed state;
pulsation detection means which detects pulsation before measurement start of the examinee;
measurement timing determination means which, when plural stable waveforms of the pulsation before the measurement start are detected, determines a measurement timing corresponding to an arbitrary point in a phase of pulsation at the measurement start based on a period of the detected pulsation waveforms;
command signal input means which inputs a command signal for execution of intraocular pressure measurement;
control means which outputs a control signal for controlling driving of the fluid blowing means based on the determined measurement timing and the input command signal; and
prediction means which predicts a deformation detection time required from output of the control signal until a predetermined corneal deformed state is detected,
wherein the measurement timing determination means determines the measurement timing based on the predicted deformation detection time.

5. The non-contact type tonometer according to claim 4, wherein the intraocular pressure measurement means obtains plural measurement values of the intraocular pressure,
the pulsation detection means successively detects pulsation after the measurement start, and
when another plural stable waveforms of the pulsation after the measurement start are newly detected, the measurement timing determination means determines the measurement timing corresponding to the arbitrary point in a phase of the pulsation after the measurement start based on a period of the newly detected pulsation waveforms.

6. A non-contact type tonometer including:
fluid blowing means which blows fluid against a cornea of an eye of an examinee;
intraocular pressure measurement means which detects a deformed state of the cornea caused by the blown fluid and determines intraocular pressure of the examinee's eye based on a result of detection of the deformed state;
first pulsation detection means which detects pulsation in a first position near an eyeball of the examinee;
second pulsation detection means which detects pulsation in a second position different from the first position;
pulsation phase shift detection means which obtains a phase shift between the pulsations detected by the first and second pulsation detection means respectively;
measurement timing determination means which determines a measurement timing based on the obtained pulsation phase shift and a detection result by the second pulsation detection means;
command signal input means which inputs a command signal for execution of intraocular pressure measurement; and
control means which outputs a control signal for controlling driving of the fluid blowing means based on the determined measurement timing and the input command signal.

7. The non-contact type tonometer according to claim 6 further including correction means which corrects, when the pulsation detected by the second pulsation detection means has changed, the determined measurement timing based on the changed pulsation.

8. The non-contact type tonometer according to claim 6, wherein the measurement timing determination means determines the measurement timing based on the previously detected pulsation by the first pulsation detection means so that intraocular pressure measurement is executed in synchronization with an intended phase point in the previously detected pulsation.

9. The non-contact type tonometer according to claim 6, wherein the measurement timing determination means determines the measurement timing based on the sequentially detected pulsation by the second pulsation detection means.

10. A non-contact type tonometer including:
fluid blowing means which blows fluid against a cornea of an eye of an examinee;
intraocular pressure measurement means which detects a deformed state of the cornea caused by the blown fluid and determines intraocular pressure of the examinee's eye based on a result of detection of the deformed state;
first pulsation detection means which detects pulsation in a first position near an eyeball of the examinee;
second pulsation detection means which detects pulsation in a second position different from the first position;
measurement timing determination means which determines a measurement timing based on the previously detected pulsation by the first pulsation detection means so that intraocular pressure measurement is executed in synchronization with an intended phase point in the previously detected pulsation, and
information means which informs that a period of the pulsation detected by the second pulsation detection means has changed after determination of the measurement timing.

* * * * *